United States Patent [19]

Ackermann et al.

[11] Patent Number: 4,611,004

[45] Date of Patent: Sep. 9, 1986

[54] 3-PHENOXYBENZYL-(2-PHENYL-2,2-ALKYLENE-ETHYL) ETHERS AND -THIOETHERS, AND THEIR USE FOR CONTROLLING PESTS

[75] Inventors: Peter Ackermann, Pfeffingen; Laurenz Gsell, Basel, both of Switzerland

[73] Assignee: Ciba-Geigy Corporation, Ardsley, N.Y.

[21] Appl. No.: 716,423

[22] Filed: Mar. 27, 1985

Related U.S. Application Data

[63] Continuation-in-part of Ser. No. 597,009, Apr. 5, 1984, abandoned.

[30] Foreign Application Priority Data

Apr. 12, 1983 [CH] Switzerland .......................... 1954/83

[51] Int. Cl.[4] .................. A01N 43/30; A01N 31/14; C07C 43/267
[52] U.S. Cl. ............................ 514/464; 558/405; 558/397; 558/392; 514/466; 558/394; 514/520; 514/712; 514/719; 549/442; 549/445; 568/49; 568/52; 568/636; 568/637
[58] Field of Search ............. 260/465 F; 568/52, 636, 568/637, 49; 549/445, 442; 514/520, 464, 712, 719, 721, 466

[56] References Cited

U.S. PATENT DOCUMENTS 4,073,812 2/1978 Bull et al. ............................ 568/637

FOREIGN PATENT DOCUMENTS 0094085 11/1983 European Pat. Off. .

Primary Examiner—Dolph H. Torrence
Attorney, Agent, or Firm—Edward McC. Roberts; Kevin T. Mansfield

[57] ABSTRACT

3-Phenoxybenzyl-(2-phenyl-2,2-alkylene-ethyl) ethers and -thioethers of the formula

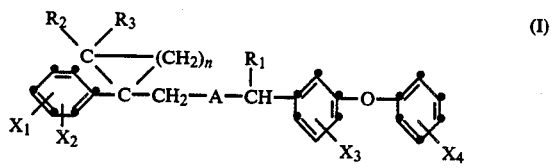

wherein
A is oxygen or sulfur,
$R_1$ is hydrogen, methyl, cyano or ethinyl,
$R_2$ and $R_3$ are hydrogen, halogen or $C_1-C_5$-alkyl,
n is 2 to 4,
$X_1$ is hydrogen, halogen, $C_1-C_5$-alkyl, $C_1-C_5$-haloalkyl, $C_1-C_5$-alkoxy or $C_1-C_5$-haloalkoxy,
$X_2$ is hydrogen, halogen or $C_1-C_5$-alkyl, or together with $X_1$ in the adjacent position is methylenedioxy, and
$X_3$ and $X_4$ are each hydrogen or halogen.

A process for producing these compounds and their use for controlling pests are described.

19 Claims, No Drawings

3-PHENOXYBENZYL-(2-PHENYL-2,2-ALKYLENE-ETHYL) ETHERS AND -THIOETHERS, AND THEIR USE FOR CONTROLLING PESTS

CROSS REFERENCE TO RELATED APPLICATION

This is a continuation-in-part of application Ser. No. 597,009 filed Apr. 5, 1984, abandoned.

The present invention relates to 3-phenoxybenzyl-(2-phenyl-2,2-alkylene-ethyl)ethers and -thioethers, to processes for producing them, and to their use for controlling pests.

The 3-phenoxybenzyl-(2-phenyl-2,2-alkylene-ethyl)ethers and -thioethers have the formula

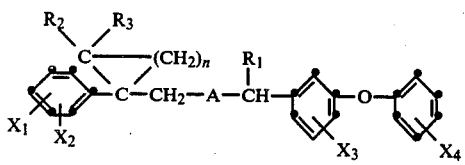

(I)

wherein
A is oxygen or sulfur,
$R_1$ is hydrogen, methyl, cyano or ethinyl,
$R_2$ and $R_3$ are hydrogen, halogen or $C_1$–$C_5$-alkyl,
n is 2 to 4,
$X_1$ is hydrogen, halogen, $C_1$–$C_5$-alkyl, $C_1$–$C_5$-haloalkyl, $C_1$–$C_5$-alkoxy or $C_1$–$C_5$-haloalkoxy,
$X_2$ is hydrogen, halogen or $C_1$–$C_5$-alkyl, or together with $X_1$ in the adjacent position is methylenedioxy, and
$X_3$ and $X_4$ are each hydrogen or halogen.

Halogen in this case is fluorine, chlorine, bromine or iodine, particularly fluorine or chlorine.

The alkyl, haloalkyl, alkoxy and haloalkoxy groups denoted by $R_2$, $R_3$, $X_1$ and $X_2$ can be straight-chain or branched-chain. Examples of such groups are, inter alia: methyl, trifluoromethyl, methoxy, difluoromethoxy, ethyl, ethoxy, propyl, isopropyl, n-butyl and n-pentyl and isomers thereof.

Preferred compounds of the formula I are those wherein
A is oxygen or sulfur,
$R_1$ is hydrogen, methyl, cyano or ethinyl,
$R_2$ and $R_3$ are each hydrogen, halogen or $C_1$–$C_5$-alkyl,
n is 2 to 4,
$X_1$ is hydrogen, halogen, $C_1$–$C_5$-alkyl, $C_1$–$C_5$-haloalkyl, $C_1$–$C_5$-alkoxy or $C_1$–$C_5$-haloalkoxy,
$X_2$ is hydrogen, halogen or $C_1$–$C_5$-alkyl, and
$X_3$ and $X_4$ are each hydrogen or halogen.

Particularly preferred compounds of the formula I are those wherein
A is oxygen or sulfur,
$R_1$ is hydrogen,
$R_2$ and $R_3$ are each hydrogen, halogen or methyl,
n is 2 to 4,
$X_1$ is hydrogen, halogen, $C_1$–$C_4$-alkyl, $C_1$–$C_4$-alkoxy, trifluoromethyl or difluoromethoxy,
$X_2$ is hydrogen, and
$X_3$ and $X_4$ are each hydrogen or halogen.

More especially preferred compounds of the formula I are those wherein
A is oxygen,
$R_1$ is hydrogen,
$R_2$ and $R_3$ are each hydrogen, halogen or methyl,
n is 2 to 4,
$X_1$ is hydrogen, halogen, methoxy or ethoxy,
$X_2$ is hydrogen, and
$X_3$ and $X_4$ are each hydrogen or halogen.

The compounds of the formula I are produced by method known per se, for example as follows:

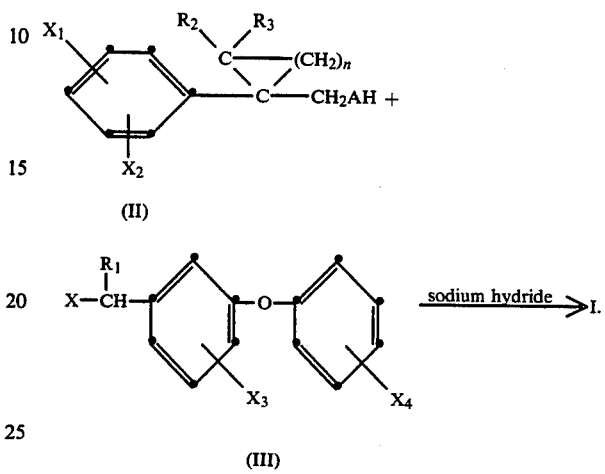

In the formulae II and III, the symbols A, $R_1$, $R_2$, $R_3$, n and $X_1$ to $X_4$ have the meanings defined under the formula I.

X in the formula III is a halogen atom, especially chlorine or bromine, or the p-toluenesulfonate group.

The reaction is performed at a reaction temperature of between $-10°$ and $+120°$ C., usually between 20° and 80° C., under normal or elevated pressure, and preferably in an inert solvent or diluent. Suitable solvents or diluents are for example: ethers and ethereal compounds, such as diethyl ether, dipropyl ether, dioxane, dimethoxyethane and tetrahydrofuran; amides, such as N,N-dialkylated carboxylic acid amides; aliphatic, aromatic as well as halogenated hydrocarbons, particularly benzene, toluene, xylenes, chloroform and chlorobenzene; nitriles, such as acetonitrile; dimethyl sulfoxide, and ketones, such as acetone and methyl ethyl ketone.

The starting materials of the formulae II and III are known, or they can be produced by methods analogous to known methods.

If homogeneous optically active starting materials are not used in producing the compounds of the formula I, these compounds are obtained as mixtures of various optically active isomers. The different isomeric mixtures can be separated by known methods into the individual isomers. The term 'compounds of the formula I' embraces both the individual isomers and the mixtures thereof.

The compounds of the formula I are suitable for controlling various pests on animals and plants. They can thus be used for controlling insects, for example of the orders: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera, and also mites and ticks of the order Acarina.

In particular, compounds of the formula I are suitable for controlling insects that damage plants, especially insects that damage plants by eating, in crops of ornamental plants and productive plants, particularly in cotton and rice crops (for example against *Spodoptera littoralis, Heliothis virescens, Nilaparvata lugens, Chilo suppressalis* and Laodelphax), and in vegetable and fruit crops (for example against *Leptinotarsa decemlineata, Myzus persicae, Laspeyresia pomonella* and *Adoxophyes reticulans*), and also for controlling soil insects (for example *Aulacophora femoralis, Chortophila brassicae, Diabrotica balteata, Pachnoda savigni* and *Scotia ypsilon*).

Active substances of the formula I have a very favourable action also against flies, for example *Musca domestica*, as well as against mosquito larvae, and against ectoparasitic mites and ticks, for example of the families: Ixodidae, Argasidae and Dermanyssidae. Furthermore, the compounds of the formula I are distinguished by a broad ovicidal and ovilarvicidal action.

The acaricidal and insecticidal action can be substantially broadened and adapted to suit the given circumstances by the addition of other insecticides and/or acaricides. Suitable additives are for example: organic phosphorus compounds, nitrophenols and derivatives thereof, formamidines, ureas, other pyrethrin-like compounds, as well as carbamates and chlorinated hydrocarbons.

Compounds of the formula I are combined particularly advantageously also with substances having a synergistic or intensifying effect on pyrethroids. Example of compounds of this type are, inter alia: piperonylbutoxide, propynyl ethers, propynyl oximes, propynyl carbamates and propynyl phosphonates, 2-(3,4-methylenedioxyphenoxy)-3,6,9-trioxaundecane (Sesamex or Sesoxane), S,S,S-tributylphosphorotrithioates and 1,2-methylenedioxy-4-(2-(octylsulfinyl)-propyl)-benzene.

The compounds of the formula I are used either in an unmodified form or preferably together with auxiliaries customarily employed in formulation practice, and are thus processed in a known manner for example into the form of emulsion concentrates, directly sprayable or dilutable solutions, diluted emulsions, wettable powders, soluble powders, dusts or granulates, and also encapsulations in for example polymeric substances. The application processes, such as spraying, atomising, dusting scattering or pouring, and likewise the type of composition, are selected to suit the objectives to be achieved and the given conditions.

The formulations, that is to say, the compositions or preparations containing the active ingredient of the formula I and optionally a solid or liquid additive, are produced in a known manner, for example by the intimate mixing and/or grinding of the active ingredients with extenders, such as with solvents, solid carriers and optionally surface-active compounds (tensides).

Suitable solvents are: aromatic hydrocarbons, preferably the fractions $C_8$ to $C_{12}$, such as xylene mixtures or substituted naphthalenes, phthalic esters, such as dibutyl- or dioctylphthalate, aliphatic hydrocarbons, such as cyclohexane or paraffins, alcohols and glycols, as well as ethers and esters thereof, such as ethanol, ethylene glycol, ethylene glycol monomethyl or -ethyl ethers, ketones such as cyclohexanone, strongly polar solvents, such as N-methyl-2-pyrrolidone, dimethyl sulfoxide or dimethylformamide, as well as optionally epoxidised vegetable oils, such as epoxidised coconut oil or soybean oil; or water.

The solid carriers used, for example for dusts and dispersible powders, are as a rule natural mineral fillers, such as calcite, talcum, kaolin, montmorillonite or attapulgite. In order to improve the physical properties, it is also possible to add highly dispersed silicic acid or highly dispersed absorbent polymers. Suitable granulated adsorptive carriers are porous types, for example pumice, ground brick, sepiolite or bentonite, and suitable nonsorbent carriers are materials such as calcite or sand. There can also be used a great number of pregranulated materials of inorganic or organic nature, such as in particular dolomite or ground plant residues.

Suitable surface-active compounds are, depending on the nature of the active ingredient of the formula I to be formulated, nonionic, cationic and/or anionic tensides having good emulsifying, dispersing and wetting properties. By 'tensides' are also meant mixtures of tensides.

Suitable anionic tensides are both so-called water-soluble soaps as well as water-soluble, synthetic, surface-active compounds.

Soaps which are applicable are the alkali metal, alkaline-earth metal or optionally substituted ammonium salts of higher fatty acids ($C_{10}$–$C_{22}$), for example the Na or K salts of oleic or stearic acid, or of natural fatty acid mixtures, which can be obtained for example from coconut oil or tallow oil. Also to be mentioned are the fatty acid-methyl-taurine salts.

So-called synthetic tensides are however more frequently used, particularly fatty sulfonates, fatty sulfates, sulfonated benzimidazole derivatives or alkylarylsulfonates. The fatty sulfonates or sulfates are as a rule in the form of alkali metal, alkaline-earth metal or optionally substituted ammonium salts, and contain an alkyl group having 8 to 22 C atoms, 'alkyl' including also the alkyl moiety of acyl groups, for example the Na or Ca salt of ligninsulfonic acid, of dodecylsulfuric acid ester or of a fatty alcohol sulfate mixture produced from natural fatty acids. Included amongst these are also the salts of sulfuric acid esters and of sulfonic acids of fatty alcohol ethylene oxide adducts. The sulfonated benzimidazole derivatives preferably contain 2 sulfonic acid groups and a fatty acid group having 8–22 C atoms. Alkylarylsulfonates are for example the Na, Ca or triethanolamine salts of dodecylbenzenesulfonic acid, of dibutylnaphthalenesulfonic acid, or of a naphthalenesulfonic acid-formaldehyde condensation product. Also suitable are corresponding phosphates, for example salts of the phosphoric ester of a p-nonylphenol-(4–14)-ethylene oxide adduct, and phospholipides.

Suitable nonionic tensides are in particular polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl moiety of the alkylphenols.

Further suitable nonionic tensides are the water-soluble polyethylene oxide adducts, which contain 20 to 250 ethylene glycol ether groups and 10 to 100 propylene glycol ether groups, with polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit. Examples of nonionic tensides which may be mentioned are: nonylphenol-polyethoxyethanols, castor oil polyglycol ethers, polypropylene/polyethyleneoxy adducts, tributylphenoxy-polyethoxyethanol, polyethylene glycol and octylphenoxy-polyethoxyethanol. Suitable also are fatty acid esters of polyoxyethylenesorbitan, such as polyoxyethylenesorbitan-trioleate.

In the case of the cationic tensides, they are in particular quanternary ammonium salts which contain as N-substituents at least one alkyl group having 8 to 22 C atoms and, as further substituents, lower, optionally halogenated alkyl, benzyl or lower hydroxyalkyl groups. The salts are preferably in the form of halides, methyl sulfates or ethyl sulfates, for example stearyl-trimethylammonium chloride or benzyldi (2-chloroethyl)ethylammonium bromide.

The tensides customarily used in formulation practice are described, inter alia, in the following publications:

"Mc Cutcheon's Detergents and Emulsifiers Annual", MC Publishing Corp., Ridgwood, N.J., 1979; and Dr. Helmut Stache "Tensid Taschenbuch", Carl Hanser Verlag, Munich/Vienna, 1981.

The pesticidal preparations contain as a rule 0.1 to 99%, particularly 0.1 to 95%, of active ingredient of the formula I, 1 to 99.9% of a solid or liquid additive, and 0 to 25%, especially 0.1 to 25%, of a tenside.

Whereas commercial products are preferably in the form of concentrated compositions, the compositions employed by the end-user are as a rule diluted.

The compositions can also contain further additives such as stabilisers, antifoam agents, viscosity regulators binders and adhesives, as well as fertilisers or other active ingredients for obtaining special effects.

FORMULATION EXAMPLES FOR LIQUID ACTIVE INGREDIENTS OF THE FORMULA I (%=PERCENT BY WEIGHT)

| 1. Emulsion concentrates | (a) | (b) | (c) |
|---|---|---|---|
| active ingredient | 25% | 40% | 50% |
| calcium dodecylbenzenesulfonate | 5% | 8% | 6% |
| castor oil-polyethylene glycol ether (36 mols of ethylene oxide) | 5% | — | — |
| tributylphenol-polyethylene glycol ether (30 mols of ethylene oxide) | — | 12% | 4% |
| cyclohexanone | — | 15% | 20% |
| xylene mixture | 65% | 25% | 20% |

Emulsions of any required concentration can be produced from concentrates of this type by dilution with water.

| 2. Solutions | (a) | (b) | (c) | (d) |
|---|---|---|---|---|
| active ingredient | 80% | 10% | 5% | 95% |
| ethylene glycol-monomethyl ether | 20% | — | — | — |
| polyethylene glycol M.W. 400 | — | 70% | — | — |
| N—methyl-2-pyrrolidone | — | 20% | — | — |
| epoxidised coconut oil | — | — | 1% | 5% |
| ligroin (boiling limits 160–190° C.) | — | — | 94% | — |

These solutions are suitable for application in the form of very small drops.

| 3. Granulates | (a) | (b) |
|---|---|---|
| active ingredient | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 4. Dusts | (a) | (b) |
|---|---|---|
| active ingredient | 2% | 5% |
| highly dispersed silicic acid | 1% | 5% |
| talcum | 97% | — |
| kaolin | — | 90% |

Dusts ready for use are obtained by the intimate mixing together of the carriers with the active ingredient.

FORMULATION EXAMPLES FOR SOLID ACTIVE INGREDIENTS OF THE FORMULA I (%=PERCENT BY WEIGHT)

| 5. Wettable powders | (a) | (b) | (c) |
|---|---|---|---|
| active ingredient | 20% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7–8 mols of ethylene oxide) | — | 2% | — |
| highly dispersed silica acid | 5% | 10% | 10% |
| kaolin | 67% | 27% | — |

The active ingredient is well mixed with the additives and the mixture is thoroughly ground in a suitable mill. Wettable powders which can be diluted with water to give suspensions of the required concentration are obtained.

| 6. Emulsion concentrate | |
|---|---|
| active ingredient | 10% |
| octylphenol polyethylene glycol ether (4–5 mols of ethylene oxide) | 3% |
| calcium dodecylbenzene sulfonate | 3% |
| castor oil polyglycol ether (36 mols of ethylene oxide) | 4% |
| cyclohexanone | 30% |
| xylene mixture | 50% |

Emulsions of the concentration required can be obtained from this concentrate by dilution with water.

| 7. Dusts | (a) | (b) |
|---|---|---|
| active ingredient | 5% | 8% |
| talcum | 95% | — |
| kaolin | — | 92% |

Dusts ready for use are obtained by mixing the active ingredient with the carrier, and grinding the mixture in a suitable mill.

| 8. Extruder granulate | |
|---|---|
| active ingredient | 10% |
| sodium lignin sulfonate | 2% |
| carboxymethyl cellulose | 1% |
| kaolin | 87% |

The active ingredient is mixed and ground with the additives, and the mixture is moistened with water. This mixture is extruded and then dried in a stream of air.

| 9. Coated granulate | |
|---|---|
| active ingredient | 3% |
| polyethylene glycol (M.W. 200) | 3% |

-continued

| 9. Coated granulate | |
|---|---|
| kaolin | 94% |

The finely ground active ingredient is evenly applied, in a mixer, to the kaolin moistened with polyethylene glycol. Dustfree coated granulates are obtained in this manner.

| 10. Suspension concentrate | |
|---|---|
| active ingredient | 40% |
| ethylene glycol | 10% |
| nonylphenolpolyethylene glycol ether (15 mols of ethylene oxide) | 6% |
| sodium lignin sulfonate | 10% |
| carboxymethyl cellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the additives. There is obtained a suspension concentrate from which can be produced, by dilution with water, suspensions of the concentration required.

EXAMPLE 1

Production of the compound No. 1 of the formula

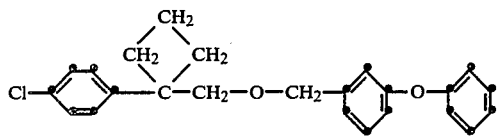

To a mixture heated to 95° C. of 1.35 g of sodium hydride and 80 ml of dimethylformamide/toluene (1:1) is added dropwise, within 15 minutes, a solution of 4.4 g of the compound of the formula

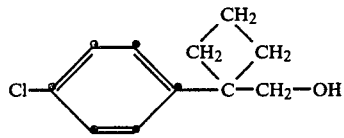

in 5 ml of dimethylformamide/toluene (1:1). After being stirred for 15 minutes at 95° C., the reaction mixture is cooled to 50° C.; there is then added dropwise, in the course of 3 hours, a solution of 6.9 g of the compound of the formula

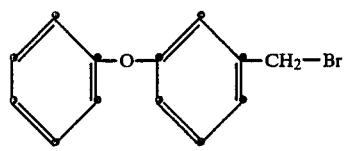

in 10 ml of dimethylformamide/toluene (1:1), and subsequently 1.35 g of potassium iodide and 0.2 g of 18-crown-6 ether are added. The reaction mixture is left to stand for 24 hours at 20° C.; saturated ammonium chloride solution is afterwards added and the mixture is extracted with ether. The ether phase is washed with a saturated sodium chloride solution, dried over magnesium sulfate and concentrated by evaporation. The product is chromatographed on silica gel with hexane/ether (5:1) as eluant to thus obtain the title compound having a refractive index of $n_D^{25°} = 1.5850$.

There are produced in an analogous manner also the following compounds of the formula I wherein A is oxygen:

| No. | $X_1$ para | $X_2$ | $X_3$ | $X_4$ | $R_1$ | $R_2$ | $R_3$ | n | Refr. index |
|---|---|---|---|---|---|---|---|---|---|
| 2 | Cl | H | 4-F | H | H | H | H | 2 | $n_D^{24°} = 1.5764$ |
| 3 | H | H | 4-F | H | H | CH$_3$ | H | 2 | $n_D^{20°} = 1.5654$ |
| 4 | H | H | H | H | H | CH$_3$ | H | 2 | $n_D^{30°} = 1.5756$ |
| 5 | Br | H | H | H | H | CH$_3$ | H | 2 | $n_D^{21°} = 1.5910$ |
| 6 | Br | H | 4-F | H | H | CH$_3$ | H | 2 | $n_D^{21°} = 1.5826$ |
| 7 | MeO | H | H | 4-F | H | H | H | 4 | $n_D^{22°} = 1.5696$ |
| 8 | MeO | H | 4-F | H | H | H | H | 4 | $n_D^{22°} = 1.5729$ |
| 9 | MeO | H | H | 4-F | H | H | H | 3 | $n_D^{22°} = 1.5714$ |
| 10 | MeO | H | H | H | H | H | H | 4 | $n_D^{21°} = 1.5821$ |
| 11 | MeO | H | H | 4-Cl | H | H | H | 3 | $n_D^{22°} = 1.5825$ |
| 12 | EtO | H | H | 4-Cl | H | H | H | 3 | $n_D^{22°} = 1.5774$ |
| 13 | EtO | H | H | 4-Br | H | H | H | 3 | $n_D^{22°} = 1.5868$ |
| 14 | EtO | H | H | H | H | H | H | 3 | $n_D^{22°} = 1.5763$ |
| 15 | MeO | H | H | 4-Br | H | H | H | 4 | $n_D^{22°} = 1.5911$ |
| 16 | Cl | H | H | 4-F | H | H | H | 3 | $n_D^{26°} = 1.5753$ |
| 17 | EtO | H | H | 4-F | H | H | H | 3 | $n_D^{25°} = 1.5650$ |
| 18 | Cl | H | H | H | H | H | H | 3 | $n_D^{25°} = 1.5833$ |
| 19 | Cl | H | H | 4-Br | H | H | H | 3 | resin |
| 20 | MeO | H | H | 4-Br | H | H | H | 3 | $n_D^{22°} = 1.5953$ |
| 21 | Cl | H | H | 4-Cl | H | H | H | 3 | $n_D^{23°} = 1.5918$ |
| 22 | Cl | H | H | H | H | H | H | 4 | $n_D^{22°} = 1.5782$ | as well as the isomers of the formulae

23 $n_D^{24°} = 1.5750$

24 $n_D^{22°} = 1.5810$

EXAMPLE 2

Insecticidal stomach-poison action: *Spodoptera littoralis*

Cotton plants are sprayed with a test solution containing 400 ppm of the compound to be tested. After the drying of the coating, larvae of *Spodoptera littoralis* (L$_3$ stage) are settled onto the plants. Two plants are used per test compound, and an evaluation of the mortality rate achieved is made after 2, 4, 24 and 48 hours. The test is carried out at 28° C. with 60% relative humidity.

Compounds according to Example 1 are 100% effective against larvae of *Spodoptera littoralis* in the above test.

EXAMPLE 3

Action against *Diabrotica balteata*

750 ml of compost soil are mixed with 150 ml of a test solution containing 3 ppm of active ingredient. Maize seedlings are potted with the treated soil in plastic pots (4 seedlings per pot of 10 cm diameter). The pots are immediately afterwards infested with 10 L$_3$ larvae of *Diabrotica balteata*. An evaluation of the results achieved is made 10 days after infestation with the larvae.

Compounds according to Example 1 are 100% effective in the above test against L₃ larvae of *Diabrotica balteata*.

EXAMPLE 4

Insecticidal stomach-poison action: *Nilaparvata lugens*

Rice plants are sprayed with a test solution containing 50 ppm of the compound to be tested. After the drying of the coating applied, larvae of *Nilaparvata lugens* (L₃ stage) are settled onto the plants. Two plants are used per test compound, and an evaluation of the mortality rate achieved is made after 24 hours. The test is carried out at 22° C. with 60 relative humidity.

Compounds according to Example 1 are 100% effective against larvae of *Nilaparvata lugens*.

What is claimed is:

1. A 3-phenoxybenzyl-(2-phenyl-2,2-alkylene-ethyl) ether of the formula

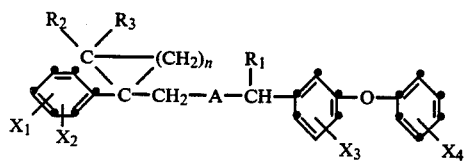

wherein
A is oxygen or sulfur,
$R_1$ is hydrogen, methyl, cyano or ethinyl,
$R_2$ and $R_3$ are hydrogen, halogen or $C_1$–$C_5$-alkyl,
n is 2 to 4,
$X_1$ is hydrogen, halogen, $C_1$–$C_5$-alkyl, $C_1$–$C_5$-haloalkyl, $C_1$–$C_5$-alkoxy or $C_1$–$C_5$-haloalkoxy,
$X_2$ is hydrogen, halogen or $C_1$–$C_5$-alkyl, or together with $X_1$ in the adjacent position is methylenedioxy, and
$X_3$ and $X_4$ are each hydrogen or halogen.

2. A compound according to claim 1, wherein
A is oxygen or sulfur,
$R_1$ is hydrogen, methyl, cyano or ethinyl,
$R_2$ and $R_3$ are each hydrogen, halogen or $C_1$–$C_5$-alkyl,
n is 2 to 4,
$X_1$ is hydrogen, halogen, $C_1$–$C_5$-alkyl, $C_1$–$C_5$-haloalkyl, $C_1$–$C_5$-alkoxy or $C_1$–$C_5$-haloalkoxy,
$X_2$ is hydrogen, halogen or $C_1$–$C_5$-alkyl, and
$X_3$ and $X_4$ are each hydrogen or halogen.

3. A compound according to claim 2, wherein
A is oxygen or sulfur,
$R_1$ is hydrogen,
$R_2$ and $R_3$ are each hydrogen, halogen or methyl,
n is 2 to 4,
$X_1$ is hydrogen, halogen, $C_1$–$C_4$-alkyl, $C_1$–$C_4$-alkoxy, trifluormethyl or difluoromethoxy,
$X_2$ is hydrogen, and
$X_3$ and $X_4$ are each hydrogen or halogen.

4. A compound according to claim 3, wherein
A is oxygen,
$R_1$ is hydrogen,
$R_2$ and $R_3$ are each hydrogen, halogen or methyl,
n is 2 to 4,
$X_1$ is hydrogen, halogen, methoxy or ethoxy,
$X_2$ is hydrogen, and
$X_3$ and $X_4$ are each hydrogen or halogen.

5. The compound according to claim 4 of the formula

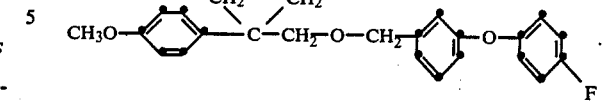

6. The compound according to claim 4 of the formula

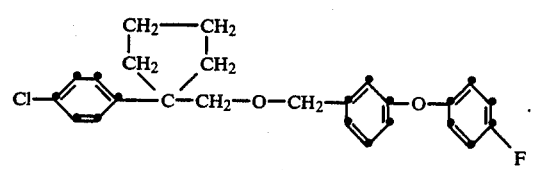

7. The compound according to claim 4 of the formula

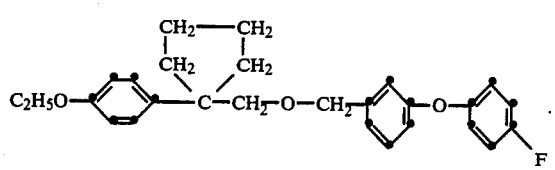

8. The compound according to claim 4 of the formula

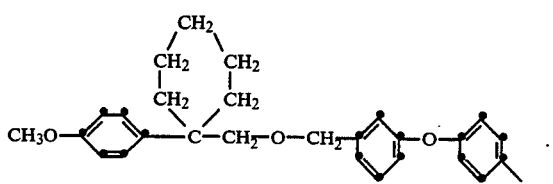

9. The compound according to claim 4 of the formula

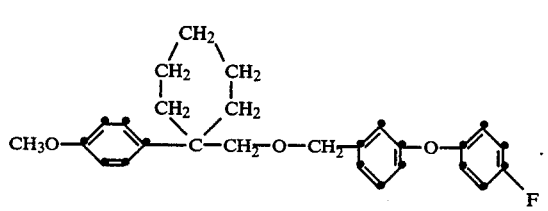

10. The compound according to claim 4 of the formula

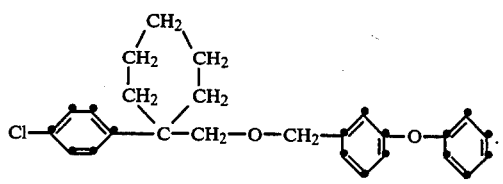

11. The compound according to claim 4 of the formula

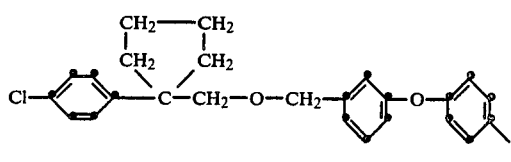

12. The compound according to claim 4 of the formula

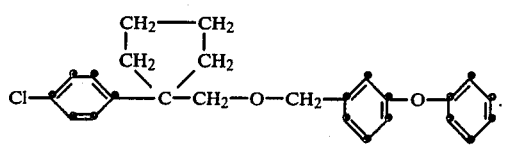

13. The compound according to claim 4 of the formula

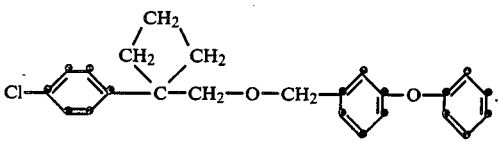

14. The compound according to claim 4 of the formula

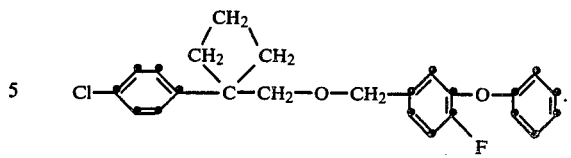

15. The compound according to claim 4 of the formula

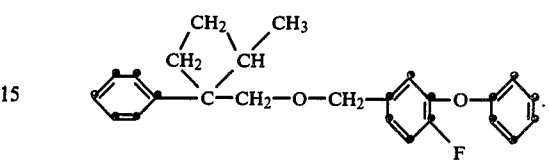

16. The compound according to claim 4 of the formula

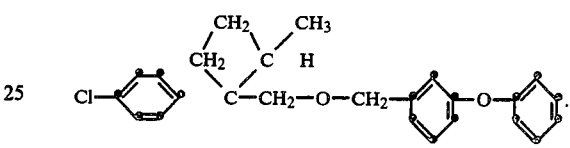

17. The compound according to claim 4 of the formula

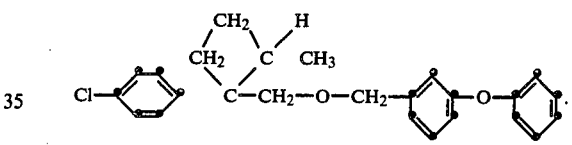

18. A pesticidal composition which contains as active ingredient a compound according to claim 1, together with solvents or solid carriers.

19. A method of controlling various insects and acarids on animals and plants, which method comprises applying thereto or to the locus thereof an effective amount of a compound according to claim 1.

* * * * *